United States Patent
Van Der Maas et al.

(10) Patent No.: US 12,297,471 B2
(45) Date of Patent: May 13, 2025

(54) MUTANT ALLELE OF THE ACO2 GENE

(71) Applicant: RIJK ZWAAN ZAADTEELT EN ZAADHANDEL B.V., De Lier (NL)

(72) Inventors: Cornelis Van Der Maas, De Lier (NL); Cornelis Haaring, De Lier (NL)

(73) Assignee: RIJK ZWAAN ZAADTEELT EN ZAADHANDEL B.V., De Lier (NL)

( * ) Notice: Subject to any disclaimer, the term of this patent is extended or adjusted under 35 U.S.C. 154(b) by 235 days.

(21) Appl. No.: 17/158,363

(22) Filed: Jan. 26, 2021

(65) Prior Publication Data

US 2021/0214707 A1   Jul. 15, 2021

Related U.S. Application Data

(63) Continuation-in-part of application No. PCT/EP2019/070535, filed on Jul. 30, 2019.

(30) Foreign Application Priority Data

Aug. 1, 2018   (WO) .................. PCT/EP2018/070905

(51) Int. Cl.
| | |
|---|---|
| C12N 9/88 | (2006.01) |
| A01H 1/04 | (2006.01) |
| C12N 15/82 | (2006.01) |
| C12Q 1/6895 | (2018.01) |

(52) U.S. Cl.
CPC ............... *C12N 9/88* (2013.01); *A01H 1/045* (2021.01); *C12N 15/8287* (2013.01); *C12Q 1/6895* (2013.01); *C12Q 2600/13* (2013.01)

(58) Field of Classification Search
None
See application file for complete search history.

(56) References Cited

U.S. PATENT DOCUMENTS

| | | | |
|---|---|---|---|
| 2011/0314569 A1 | 12/2011 | Bendahmane et al. | |
| 2014/0359896 A1* | 12/2014 | Bendahmane et al. | .. A01H 5/08 435/232 |

OTHER PUBLICATIONS

Chen et al. "An ACC Oxidase Gene Essential for Cucumber Carpel Development" 2016 Mol. Plant 9:1315-1327. (Year: 2016).*
UniProtKB Accession A0A0A0KH90_CUCSA (*Cucumis sativus* (cucumber) ACC oxidase 2 sequence version 15 dated Feb. 15,2017; 2 pages) (Year: 2017).*
Database Accession No. EMBL AF033582, Cucumis sativus ACC oxidase 2 (Cs-ACO2) mRNA, partial ods (Apr. 8, 1998).
Database Accession No. EMBL KGN49070, *Cucumis sativus* (cucumber) ACC oxidase 2 (Oct. 29, 2014).
Huiming Chen, et al., An ACC Oxidase Gene Essential for Cucumber Carpel Development, Molecular Plant 9, 1315-1327, Sep. 2016.
Qiao-Hong Duan, et al., Stamen development in *Arabidopsis* is arrested by organ-specific overexpression of a cucumber ethylene synthesis gene CsACO2, Planta (2008) 228:4:537-543.
Anat Kahana, et al., Expression of ACC oxidase genes differs among sex genotypes and sex phases in cucumber, Plant Molecular Biology (1991) 41:517-528.
Int'l Search Report and Written Opinion dated Aug. 29, 2019 issued in Int'l Application No.

* cited by examiner

*Primary Examiner* — Matthew R Keogh
*Assistant Examiner* — Rebecca Stephens
(74) *Attorney, Agent, or Firm* — Duane Morris LLP; Thomas J. Kowalski

(57) ABSTRACT

The present invention relates to a mutant ACO2 gene allele, which leads to a plant of the family of Cucurbitacea, in particular a cucumber plant producing only male flowers. The invention also relates to a plant of the family of Cucurbitacea, in particular a cucumber plant, comprising the mutant ACO2 gene allele. The mutant ACO2 allele provides plants that only produce male flowers. The invention further relates to the use of the mutant allele of the ACO2 gene for the identification and development of a plant of the family of Cucurbitacea, in particular a cucumber plant, producing only male flowers.

13 Claims, No Drawings

Specification includes a Sequence Listing.

SEQUENCE LISTING

<160> NUMBER OF SEQ ID NOS: 6

<210> SEQ ID NO 1
<211> LENGTH: 963
<212> TYPE: DNA
<213> ORGANISM: Cucumis sativus
<220> FEATURE:
<223> OTHER INFORMATION: Wildtype ACO2

```
<400> SEQUENCE: 1
atggagatgg atttccctgt catcaacatg aacaacctca atggcgaaag cagagtatct      60
gtcctgaacc aaatcaacga cgcctgcgaa aactgggggtt tttttgagtt ggtgaatcat    120
gggataccac atgagctgat ggacaaagtg gagaagatga caaaggaaca ttatagaaag    180
tgcatggagc agaggtttaa agaaatggta gcttccaaag ggttggattc agtggaaact    240
gagatcaacg acactgattg ggaaagcact ttttttttac gccatcttcc agtttcaaac    300
atgtcagaaa ttggtgatct ggatgaggag tacaagaagg tgatgaagga atttgcagct    360
gaactggaga aattagcgga ggaaattctg aacttgttgt gtgagaatct tgggcttgaa    420 aagggggtatt tgaaaaaagt gttttatgga tcaaaaggcc caaactttgg gacaaaagtt    480
agcaattacc ctccatgtcc taaacctgag cttattaaag gacttagagc ccataccgat    540
gctggtggtc ttattcttct gtttcaagat gataaagtga gtgggcttca gctgctcaaa    600
gatggaaaat gggttgatgt tcctccgatg catcactcca ttgttatcaa tttaggagac    660
cagcttgaag taataacaaa tggaaaatac aagagtgtaa tgcacagagt gatagcacag    720
gaggatggaa acagaatgtc gatagcatca ttctacaatc caggaaacga cgccgtaatc    780
tatccggcgc cggcgctggt cgagggagag caggagaaaa ccaaacttta cccaaaattt    840
gtgttcgatg attacatgaa gctgtatatg gggcttaagt ttcaagcaaa agagccaagg    900
tttgaggcca tgaaagccat ggagtccacc aatatcaata tgggtccaat tgcaactgtc    960
tga                                                                 963

<210> SEQ ID NO 2
<211> LENGTH: 320
<212> TYPE: PRT
<213> ORGANISM: Cucumis sativus
<220> FEATURE:
<223> OTHER INFORMATION: Wildtype ACO2

<400> SEQUENCE: 2

Met Glu Met Asp Phe Pro Val Ile Asn Met Asn Asn Leu Asn Gly Glu
1               5                   10                  15

Ser Arg Val Ser Val Leu Asn Gln Ile Asn Asp Ala Cys Glu Asn Trp
            20                  25                  30

Gly Phe Phe Glu Leu Val Asn His Gly Ile Pro His Glu Leu Met Asp
        35                  40                  45

Lys Val Glu Lys Met Thr Lys Glu His Tyr Arg Lys Cys Met Glu Gln
    50                  55                  60

Arg Phe Lys Glu Met Val Ala Ser Lys Gly Leu Asp Ser Val Glu Thr
65                  70                  75                  80

Glu Ile Asn Asp Thr Asp Trp Glu Ser Thr Phe Phe Leu Arg His Leu
                85                  90                  95

Pro Val Ser Asn Met Ser Glu Ile Gly Asp Leu Asp Glu Glu Tyr Lys
            100                 105                 110

Lys Val Met Lys Glu Phe Ala Ala Glu Leu Glu Lys Leu Ala Glu Glu
        115                 120                 125

Ile Leu Asn Leu Leu Cys Glu Asn Leu Gly Leu Glu Lys Gly Tyr Leu
    130                 135                 140

Lys Lys Val Phe Tyr Gly Ser Lys Gly Pro Asn Phe Gly Thr Lys Val
145                 150                 155                 160

Ser Asn Tyr Pro Pro Cys Pro Lys Pro Glu Leu Ile Lys Gly Leu Arg
                165                 170                 175
```

```
Ala His Thr Asp Ala Gly Gly Leu Ile Leu Leu Phe Gln Asp Asp Lys
            180                 185                 190

Val Ser Gly Leu Gln Leu Leu Lys Asp Gly Lys Trp Val Asp Val Pro
        195                 200                 205

Pro Met His His Ser Ile Val Ile Asn Leu Gly Asp Gln Leu Glu Val
    210                 215                 220

Ile Thr Asn Gly Lys Tyr Lys Ser Val Met His Arg Val Ile Ala Gln
225                 230                 235                 240

Glu Asp Gly Asn Arg Met Ser Ile Ala Ser Phe Tyr Asn Pro Gly Asn
                245                 250                 255

Asp Ala Val Ile Tyr Pro Ala Pro Ala Leu Val Glu Gly Gln Glu
            260                 265                 270

Lys Thr Lys Leu Tyr Pro Lys Phe Val Phe Asp Asp Tyr Met Lys Leu
        275                 280                 285

Tyr Met Gly Leu Lys Phe Gln Ala Lys Glu Pro Arg Phe Glu Ala Met
    290                 295                 300

Lys Ala Met Glu Ser Thr Asn Ile Asn Met Gly Pro Ile Ala Thr Val
305                 310                 315                 320

<210> SEQ ID NO 3
<211> LENGTH: 963
<212> TYPE: DNA
<213> ORGANISM: Cucumis sativus
<220> FEATURE:
<223> OTHER INFORMATION: Mutant ACO2
<220> FEATURE:
<221> NAME/KEY: misc_feature
<222> LOCATION: 278
<223> OTHER INFORMATION: /note="n = a or t or c or g"

<400> SEQUENCE: 3
atggagatgg atttccctgt catcaacatg aacaacctca atggcgaaag cagagtatct      60
gtcctgaacc aaatcaacga cgcctgcgaa aactggggtt ttttgagtt ggtgaatcat      120 gggataccac atgagctgat ggacaaagtg agaagatga caaaggaaca ttatagaaag      180
tgcatggagc agaggtttaa agaaatggta gcttccaaag ggttggattc agtggaaact      240
gagatcaacg acactgattg ggaaagcact ttttttnac gccatcttcc agtttcaaac      300
atgtcagaaa ttggtgatct ggatgaggag tacaagaagg tgatgaagga atttgcagct      360
gaactggaga aattagcgga ggaaattctg aacttgttgt gtgagaatct tgggcttgaa      420 aagggggtatt tgaaaaaagt gttttatgga tcaaaaggcc caactttggg acaaaagtt      480 agcaattacc ctccatgtcc taaacctgag cttattaaag gcttagagc ccataccgat      540 gctggtggtc ttattcttct gtttcaagat gataaagtga gtgggcttca gctgctcaaa      600
gatggaaaat gggttgatgt tcctccgatg catcactcca ttgttatcaa tttaggagac      660
cagcttgaag taataacaaa tggaaaatac aagagtgtaa tgcacagagt gatagcacag      720
gaggatggaa acagaatgtc gatagcatca ttctacaatc caggaaacga cgccgtaatc      780
tatccggcgc cggcgctggt cgagggagag caggagaaaa ccaaacttta cccaaaattt      840
gtgttcgatg attacatgaa gctgtatatg gggcttaagt ttcaagcaaa agagccaagg      900
tttgaggcca tgaaagccat ggagtccacc aatatcaata tgggtccaat tgcaactgtc      960
tga                                                                    963

<210> SEQ ID NO 4
<211> LENGTH: 113
<212> TYPE: PRT
```

<213> ORGANISM: Cucumis sativus
<220> FEATURE:
<223> OTHER INFORMATION: Mutant ACO2

<400> SEQUENCE: 4

```
Met Glu Met Asp Phe Pro Val Ile Asn Met Asn Asn Leu Asn Gly Glu
1               5                   10                  15

Ser Arg Val Ser Val Leu Asn Gln Ile Asn Asp Ala Cys Glu Asn Trp
            20                  25                  30

Gly Phe Phe Glu Leu Val Asn His Gly Ile Pro His Glu Leu Met Asp
        35                  40                  45

Lys Val Glu Lys Met Thr Lys Glu His Tyr Arg Lys Cys Met Glu Gln
50                  55                  60

Arg Phe Lys Glu Met Val Ala Ser Lys Gly Leu Asp Ser Val Glu Thr
65                  70                  75                  80

Glu Ile Asn Asp Thr Asp Trp Glu Ser Thr Phe Phe Tyr Ala Ile Phe
                85                  90                  95

Gln Phe Gln Thr Cys Gln Lys Leu Val Ile Trp Met Arg Ser Thr Arg
            100                 105                 110

Arg
```

<210> SEQ ID NO 5
<211> LENGTH: 154
<212> TYPE: DNA
<213> ORGANISM: Cucumis sativus
<220> FEATURE:
<223> OTHER INFORMATION: Wildtype marker CS05484

<400> SEQUENCE: 5

| aatggtagct tccaaagggt tggattcagt ggaaactgag atcaacgaca ctgattggga | 60 |
| aagcactttt ttttacgcc atcttccagt ttcaaacatg tcagaaattg gtgatctgga | 120 |
| tgaggagtac aagaaggtga tgaaggaatt tgca | 154 |

<210> SEQ ID NO 6
<211> LENGTH: 154
<212> TYPE: DNA
<213> ORGANISM: Cucumis sativus
<220> FEATURE:
<223> OTHER INFORMATION: Mutant marker CS05484
<220> FEATURE:
<221> NAME/KEY: misc_feature
<222> LOCATION: 75
<223> OTHER INFORMATION: /note="n = a or c or t or g"

<400> SEQUENCE: 6

| aatggtagct tccaaagggt tggattcagt ggaaactgag atcaacgaca ctgattggga | 60 |
| aagcactttt ttttnacgcc atcttccagt ttcaaacatg tcagaaattg gtgatctgga | 120 |
| tgaggagtac aagaaggtga tgaaggaatt tgca | 154 |

MUTANT ALLELE OF THE ACO2 GENE

RELATED APPLICATIONS AND INCORPORATION BY REFERENCE

This application is a continuation-in-part application of international patent application Serial No. PCT/EP2019/070535 filed 30 Jul. 2019, which published as PCT Publication No. WO 2020/025632 on 6 Feb. 2020, which claims benefit of international patent application Serial No. PCT/EP2018/070905 filed 1 Aug. 2018.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE STATEMENT

The instant application contains a Sequence Listing which has been submitted electronically and is hereby incorporated by reference in its entirety. Said ASCII copy, is named Y7954-00478SL.txt and is 8 kbytes in size.

FIELD OF THE INVENTION

The present invention relates to a mutant allele of the ACO2 gene that determines the sex type of the flowers in Cucurbitacea, in particular in cucumber (*Cucumis sativus*), a plant having the mutant allele, and to methods for identifying and developing such plant.

BACKGROUND OF THE INVENTION

Cucumber plants of the species *Cucumis sativus* belong to the genus *Cucumis*, which contains not only the important food crop cucumber, *Cucumis sativus*, but also a variety of melon types, mostly included in *Cucumis melo*, as well as several other, less well-known *Cucumis* species. *Cucumis* is part of the large Cucurbitaceae family.

Cucumber plants are thought to have originated in Asia, they were domesticated early and have been cultivated for thousands of years in African and Asian countries. Cucumbers are presently cultivated worldwide in a large variety of types, which typically differ in size, color, and skin type. Cucumber production is most successful in a relatively warm climate as it prefers temperatures between about 18-25° C. Cucumber is an annual, herbaceous, diploid plant species with seven pairs of chromosomes.

The ratio of the male and the female flowers on a cucumber plant can vary per genotype and based on the ratio, five different types are distinguished; monoecious, gynoecious, andromonoecious, hermaphrodite, and androecious. A monoecious plant has both female and male flowers, a gynoecious plant has only female flowers, andromonoecious plants have male and bisexual flowers, hermaphrodite plants have only bisexual flowers and androecious plants have only male flowers.

Sex expression of flowers in cucumbers is genetically controlled by three major genes known in the art, named the F (female) and M (andromonoecious) and A (androecious) genes. The F gene promotes femaleness and is partially dominant, the M gene influences the bisexuality of flowers, "mm" (recessive allele m) plants have bisexual flowers instead of female flowers. Together, F and M interact to produce gynoecious (F-M-) or monoecious (ffM-) or hermaphroditic (FFmm) or andromonoecious (ffmm) sex phenotypes. Another gene, A, works in combination with F. Plants are androecious when both A and F are present as recessive alleles.

In modern horticulture, mostly gynoecious cucumber cultivars are used that produce only female flowers, thereby facilitating an optimal yield, because only female flowers can develop into fruits of marketable quality. To obtain these type of cucumber cultivars, there are different systems that can be used for producing cucumber seed, but using a gynoecious line and crossing it with another gynoecious line to produce cucumber hybrids is one of the most common systems. Preferably those two gynoecious inbred lines are homozygous for the F gene, because that makes the resulting hybrids also homozygous for F and thereby more stable for the gynoecious sex expression (as compared to hybrids resulting from gynoecious x monoecious line). To maintain a gynoecious line of cucumber or to cross two gynoecious lines, male flowers are induced by spraying with GA or silver nitrate.

Sex expression can also be modified by hormonal (mainly by ethylene), and environmental (nitrogen levels, light intensity, night temperature) factors. The plant hormone ethylene is known to contribute to the control of flower sex phenotype of cucurbits, and it has been used to in horticulture to induce female flowers. The biosynthesis of ethylene consists of the following steps. Methionine is converted into S-adenosylmethionine (SAM), SAM is converted into 1-aminocyclopropane-1-carboxylate (ACC) and ACC is oxidized to ethylene. This last step, the oxidation to ethylene, is carried out by 1-aminocyclopropane-1-carboxylate oxidase (ACC oxidase or ACO).

Citation or identification of any document in this application is not an admission that such document is available as prior art to the present invention.

SUMMARY OF THE INVENTION

It is an object of the present invention to provide a plant of the family of Cucurbitacea, in particular a cucumber plant, that produces only male flowers, as well as methods and markers to identify and/or develop such plant. A plant that produces only male flowers is in particular suitable as a pollinator plant in breeding programs and hybrid seed production.

The present inventors identified a linkage between a deletion of a single nucleotide in the ACO2 gene and the ability of producing only male flowers (also known as maleness) in cucumber plants.

The ACO2 gene may comprise two domains, the so-called DIOX_N domain and the 20G_Fell_Oxy domain. The deletion found by the present inventors is located in the DIOX_N domain.

Cucumber plants that comprise the deletion homozygously produce only male flowers (androecious plants). Cucumber plants that comprise the mutation heterozygously can produce male and female flowers.

Next to cucumber (*Cucumis sativus*), maleness can also be affected by modifying the ACO2 gene in other crops that are member of the Cucurbitacea plant family such as for example melon (*Cucumis melo*), watermelon (*Citrullus lanatus*), *Cucurbita pepo* (e.g. pumpkin and squash), *Cucurbita maxima*, and *Cucurbita moschata*. Thus, where herein is referred to the wildtype nucleotide sequence of the cucumber ACO2 gene or the wildtype amino acid sequence of the cucumber ACO2 protein, this can be replaced with the wildtype nucleotide sequence of the ACO2 gene and the wildtype amino acid sequence of the ACO2 protein, respectively, of any one of the Cucurbitacea. By using the wildtype sequence of the ACO2 gene of Cucumber (SEQ ID No: 1) the skilled person can readily identify homologs in other species of the Cucurbitaceae.

The invention thus relates to a mutant allele of the ACO2 gene which may comprise a mutation in the DIOX_N domain of the wild type ACO2 gene having the nucleotide sequence of SEQ ID NO: 1 or a wildtype ACO2 gene having a nucleotide sequence that shows at least 85%, 90%, 95%, or 99% sequence identity to SEQ ID NO: 1, wherein the mutation if homozygously present in the genome of a plant of the family of Cucurbitacea, in particular in a cucumber plant, results in a plant producing only male flowers.

The mutant allele of the ACO2 gene as used herein refers to a changed or mutant nucleotide sequence of the ACO2 gene as compared to the wild type nucleotide sequence of the ACO2 gene. The change or mutation can be any change or mutation, including but not limited to a deletion. The wild type allele of the ACO2 gene is shown by SEQ ID NO: 1, see Table 1. The mutant allele of the ACO2 gene, that causes a cucumber plant to produce only male flowers if said mutant allele is homozygously present in the cucumber plant, is shown in SEQ ID NO: 3, see also Table 1.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53 (c) EPC and Rule 28 (b) and (c) EPC. All rights to explicitly disclaim any embodiments that are the subject of any granted patent(s) of applicant in the lineage of this application or in any other lineage or in any prior filed application of any third party is explicitly reserved. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DEPOSIT

Seeds of cucumber *Cucumis sativus* EX5016-27-103 that comprise the ACO2 mutant allele homozygously, were deposited with NCIMB Ltd, Ferguson Building, Craibstone Estate, Bucksburn, Aberdeen AB21 9YA, UK on 15 Mar. 2018 under deposit accession number NCIMB 42987. The Deposit with NCIMB Ltd, under deposit accession number NCIMB 42987 was made and accepted pursuant to the terms of the Budapest Treaty. Upon issuance of a patent, all restrictions upon the deposit will be removed, and the deposit is intended to meet the requirements of 37 CFR §§ 1.801-1.809. The deposit will be irrevocably and without restriction or condition released to the public upon the issuance of a patent and for the enforceable life of the patent. The deposit will be maintained in the depository for a period of 30 years, or 5 years after the last request, or for the effective life of the patent, whichever is longer, and will be replaced if necessary during that period.

DETAILED DESCRIPTION OF THE INVENTION

The term "allele" as used herein refers to a variant form of a gene, that can be detected by genetic analysis or by the phenotype it affects.

The term "wild type" as used herein refers in general to the form of an organism, gene, protein, or trait as it would occur in nature, as opposed to a mutated or modified form. In this application "wild type" refers specifically to the naturally occurring form of the ACO2 gene and the naturally occurring form of the ACO2 protein. The naturally occurring forms of the ACO2 gene and ACO2 protein are shown in Table 1.

The terms "mutant", "mutant allele", "modified allele", "mutated ACO2 gene" and "modified ACO2 gene" as used herein refer to one or more nucleotide changes in the wild type allele of the ACO2 gene that lead to a mutant or modified version of the wild type allele of the gene. The mutation or modification can be any mutation or modification, including but not limited to a deletion.

The term maleness as used herein refers to the production of only male flowers, also further referred herein as the trait of the invention, is caused by a mutant ACO2 allele which may comprise a mutation in the wild type sequence SEQ ID NO: 1. More specifically the mutation that causes the trait of the invention is a deletion in the DIOX_N domain. The trait is inherited in a recessive manner.

The word "trait" in the context of this application refers to the phenotype of the plant. In particular, the word "trait" refers to the trait of the invention, more in particular to the trait of producing only male flowers in a plant of the family of Cucurbitacea, in particular in a cucumber plant.

A mutation is defined herein as the changing of the sequence of a gene, resulting in a variant form (allele) of a gene that may be transmitted to subsequent generations, caused by the alteration of single base units in DNA, or the deletion, insertion, or rearrangement of larger sections of genes or chromosomes. A modification is used herein as a synonym of mutation.

An indel as defined in this invention is a term for the insertion or the deletion of bases in the DNA of an organism, in this case a cucumber (*Cucumis sativus*) plant. If an indel occurs in coding regions of the genome, it will produce a frameshift mutation, unless the length of an indel is a multitude of 3.

In one embodiment, the mutation in the DIOX_N domain of the nucleotide sequence SEQ ID NO: 1 leads to a change in the amino acid sequence of SEQ ID NO: 2. The wild type amino acid sequence of the ACO2 gene, SEQ ID NO: 2, is shown in Table 1. The mutation leads to mutant amino acid sequence SEQ ID NO: 4, also shown in Table 1.

In one embodiment, the mutation in the DIOX_N domain of the nucleotide sequence SEQ ID NO: 1 leads to a premature stop codon. A stop codon is a nucleotide triplet, or codon, that signals the termination of translation into proteins. The mutation in the DIOX_N domain of the nucleotide sequence leads to a premature stop codon, or a so-called "nonsense" codon in the transcribed mRNA and eventually in a truncated, incomplete and usually non-functional protein.

In one embodiment, the mutation in the DIOX_N domain of the nucleotide sequence SEQ ID NO: 1 may comprise a deletion.

In particular, the deletion causes a frameshift. A frameshift is a change in the open reading frame resulting in a completely different translation of the amino acid sequence into protein. The earlier in the sequence the deletion occurs, the more altered the protein will become. A frameshift mutation will also change the site of the first stop codon ("UAA", "UGA" or "UAG") encountered in the sequence. The polypeptide being created as a consequence of the frame shift could be abnormally short or abnormally long, and will most likely not be functional.

In one embodiment, the mutation in the DIOX_N domain of the nucleotide sequence SEQ ID NO: 1 may comprise a deletion of at least a single thymine nucleotide. The mutant allele of the ACO2 gene may comprise nucleotide sequence SEQ ID NO: 3. The difference between wild type nucleotide sequence SEQ ID NO: 1 and the mutant nucleotide sequence SEQ ID NO: 3 is the deletion of a thymine nucleotide.

In one embodiment, the mutation in the DIOX_N domain of the nucleotide sequence SEQ ID NO: 1 is a deletion of the nucleotide on position 278 in the wild type nucleotide sequence of SEQ ID NO: 1.

In one embodiment, the mutant allele of the ACO2 gene may comprise SEQ ID NO: 3.

The invention further relates to the use of the mutant allele of the ACO2 gene for developing cucumber plants that produce only male flowers. The mutant allele of the ACO2 gene as described herein can be introduced into a cucumber plant by using modern techniques, such as for instance the CRISPR/Cas system, as well as by using traditional transgenic methods.

The invention further relates to the use of the mutant allele of the ACO2 gene, which is as found in seeds that were deposited under accession number NCIMB 42987, for conferring maleness in a cucumber plant.

The invention also relates to the use of a cucumber plant, as a recipient of the mutant allele of the ACO2 gene, which mutant allele is as found in seeds that were deposited under accession number NCIMB 42987.

The invention also relates to a plant of the family of Cucurbitacea, in particular a cucumber plant, which may comprise the mutant allele of the ACO2 gene of the present invention. When the mutation is homozygously present in the genome of a plant of the family of Cucurbitacea, in particular a cucumber plant, the plant produces only male flowers.

The trait caused by the mutant allele of the ACO2 gene is recessive, which means that the trait will only be expressed if the allele is present homozygously.

Thus in one embodiment the plant of the family of Cucurbitacea, in particular the cucumber plant, may comprise the mutant allele of the ACO2 gene homozygously. Such a plant produces only male flowers.

If the mutant allele of the ACO2 gene is present heterozygously, the trait will not be expressed, because of it being recessive. The recessive nature of the maleness trait inferred by the mutant allele of the ACO2 gene makes it very suitable for its use in cucumber hybrid seed production. Cucumber hybrid varieties preferably should produce female flowers, since those develop into cucumber fruit. Using one cucumber parent line, as a pollinator, which may comprise the ACO2 mutant allele homozygously, would result in a cucumber hybrid which may comprise the ACO2 gene heterozygously and therefore not expressing the maleness trait. Treatments of gynoecious cucumber lines with GA or silver nitrate to induce male flowers would be unnecessary.

Although there are other genes related to sex expression of cucumber flowers, if the mutant ACO2 allele of the present invention is present homozygously, the maleness trait will be expressed and the cucumber plant will only produce male flowers, both in the main stem and the lateral shoots.

A plant having the mutant allele of the ACO2 gene in heterozygous state is, however, still a plant of the invention since such a plant may be a potential source of the mutant allele of the ACO2 gene. When crossed with another plant that optionally also has the mutant allele either homozygously or heterozygously, or when crossed with itself, it can result in progeny plants that have the mutant allele homozygously and show the trait of producing only male flowers.

In one embodiment the plant of the family of Cucurbitacea, in particular the cucumber plant, of the invention is an agronomically elite plant.

In the context of this invention, an agronomically elite plant is a plant having a genotype that as a result of directed crossing and selection by human intervention results into an accumulation of distinguishable and desirable agronomic traits which allow a producer to harvest a product of commercial significance. It is thus a cultivated plant. In the course of breeding a new cucumber plant carrying the mutant ACO2 allele, desirable agronomic traits may be introduced into said cucumber plant independently of the mutant ACO2 gene.

The plant of the invention may be a plant of an inbred line, a hybrid, a doubled haploid, or a plant of a segregating population. As used herein, a plant of an inbred line is a plant of a population of plants that is the results of three or more rounds of selfing, or backcrossing; or which plant is double haploid. An inbred line may e.g. be a parent line used for the production of a commercial hybrid.

The current invention also relates to the use of a cucumber plant of the present invention as a crop, as a source of seed or as a source of propagation material.

The current invention also relates to a cell of a plant of the family of Cucurbitacea, in particular a cucumber plant, of the invention, which cell may comprise the mutant ACO2 allele of the invention.

The plant of the family of Cucurbitacea, in particular the cucumber plant, which may comprise a mutant ACO2 allele and thus a cell thereof is obtainable by crossing a plant of the family of Cucurbitacea, in particular a cucumber plant, which may comprise a mutant ACO2 allele, wherein the ACO2 allele may comprise a mutation in the DIOX_N domain of the wild type ACO2 gene nucleotide sequence of SEQ ID NO: 1, with a second plant of the family of Cucurbitacea, in particular a cucumber plant. For cucumber, the mutation in the DIOX_N domain is preferably a deletion of the nucleotide on position 278 in the wild type nucleotide sequence of SEQ ID NO: 1 as found in seeds that were deposited under accession number NCIMB 42987.

The invention further relates to a Cucurbitacea seed, in particular a cucumber seed, which may comprise the mutant allele of the ACO2 gene of the invention. The plant that can be grown from the seed also may comprise the mutant allele of the ACO2 gene of the invention. If the mutation is homozygously present, the plant produces only male flowers.

The invention also relates to a method for seed production which may comprise growing a plant from seed of the invention, allowing the plant to produce seed by allowing pollination to occur, and harvesting the seed. Production of the seed is suitably done by crossing or selfing.

Furthermore, the invention also relates to the use of Cucurbitacea seed, in particular cucumber seed, which seed may comprise a mutant ACO2 allele, wherein the mutant allele may comprise a mutation in the DIOX_N domain of the wild type ACO2 gene nucleotide sequence of SEQ ID NO: 1, for transferring the trait of producing only male flowers into another plant of the family of Cucurbitacea, in particular a cucumber plant.

The invention also relates to the use of seeds that were deposited under accession number NCIMB 42987, for transferring maleness into another cucumber plant.

Plants that comprise the mutant allele of the ACO2 gene of the invention homozygously can only act as male parents in any cross with other cucumber plants, unless they are treated with ethrel or other plant hormones.

The invention furthermore relates to hybrid seed and to a method for producing such hybrid seed which may comprise crossing a first parent plant with a second parent plant and harvesting the resultant hybrid seed, wherein said first parent plant and/or said second parent plant has the mutant allele of the ACO2 gene of the invention. A hybrid plant resulting from growing the resulting seed that may comprise the mutant allele of the ACO2 gene of the invention, is also a plant of the invention.

The invention also relates to propagation material which may comprise the mutant allele of the ACO2 gene of the invention, wherein the propagation material is selected from a microspore, pollen, an ovary, an ovule, an embryo, an embryo sac, an egg cell, a cutting, a root, a hypocotyl, a cotyledon, a stem, a leaf, a flower, an anther, a seed, a meristematic cell, a protoplast, or a cell, or a tissue culture thereof.

In one embodiment, the propagation material may comprise the mutant allele of the ACO2 gene of the invention homozygously, wherein the propagation material is selected from a microspore, pollen, ovary, ovule, embryo, embryo sac, egg cell, cutting, root, hypocotyl, cotyledon, stem, leaf, flower, anther, seed, meristematic cell, protoplast, or cell, or tissue culture thereof.

As part of the invention is considered the use of a cucumber plant as a crop, which cucumber plant which may comprise the mutant allele of the ACO2 gene as found in a cucumber plant grown from seed deposited under accession number NCIMB 42987.

Also related to the invention is the use of a cucumber plant which may comprise the mutant allele of the ACO2 gene as found in a cucumber plant grown from seed as deposited under accession number NCIMB 42987, as a source of seed.

Furthermore related is the use of a cucumber plant which may comprise the mutant allele of the ACO2 gene as found in a cucumber plant grown from seed as deposited under accession number NCIMB 42987, as a source of propagating material.

Also related is the use of a cucumber plant which may comprise the mutant allele of the ACO2 gene as found in a cucumber plant grown from seed as deposited under accession number NCIMB 42987, for consumption. A food product or a processed food product, which may comprise the Cucurbitacea, in particular cucumber, fruit, or a part thereof, that has the mutant allele of the invention, is also considered part of the invention. The food product may have undergone one or more processing steps. Such a processing step might comprise but is not limited to any one of the following treatments or combinations thereof: peeling, cutting, washing, juicing, cooking, cooling. The processed form that may be obtained is also part of the invention.

The invention further relates to a marker for identifying a cucumber plant which may comprise the mutant allele of the ACO2 gene, wherein the marker identifies a deletion of a nucleotide on position 278 of the wild type allele of the ACO2 gene nucleotide sequence of SEQ ID NO: 1. A skilled person also knows how to develop other markers based on the information described in the present invention, that are linked with the mutant ACO2 allele and could therefore be used to identify a cucumber plant which may comprise the mutant ACO2 allele.

The invention also relates to a method for producing or obtaining a plant that produces only male flowers, wherein the genome of the plant may comprise the mutant allele of the ACO2 gene of the invention homozygously, which may comprise;

a) crossing a plant which may comprise the mutant allele of the ACO2 gene of the invention with a second plant which may comprise or not comprising the mutant allele of the ACO2 gene of the invention, to obtain an F1 population;

b) optionally performing one or more rounds of selfing and/or crossing a plant from the F1 to obtain a further generation population;

c) selecting a plant that produces only male flowers and may comprise the mutant allele of the ACO2 gene of the invention homozygously.

In one embodiment, selection for plants having the trait of producing only male flowers is done in the F1 or any further generation by using as a marker the mutant ACO2 allele sequence SEQ ID NO: 3. In another aspect of the invention selection for the trait of the invention is started in the F2 of a cross or alternatively of a backcross. Selection of plants in the F2 can be done phenotypically as well as by using the said marker(s) which directly or indirectly detect the mutant allele of the ACO2 gene underlying the trait.

In one embodiment selection for plants having the trait of producing only male flowers is started in the F3 or a later generation The mutant allele of the ACO2 gene of the invention can be introduced into another plant through commonly used breeding techniques, such as crossing and selection, when the plants are sexually compatible. To obtain a plant which has the mutant allele of the ACO2 gene homozygously, a plant which may comprise the mutant allele heterozygously can be selfed or can be crossed with another plant which may comprise at least one mutant allele of the ACO2 gene.

Such introduction can be from a plant of the same species, that can be crossed easily, or from a plant from a related species. Difficulties in crossing can be overcome through techniques known in the art, such as embryo rescue.

Alternatively, the mutant allele of the ACO2 gene can be transferred from another, sexually incompatible plant for example by using a transgenic approach. Techniques that can suitably be used comprise general plant transformation techniques known to the skilled person, such as the use of an *Agrobacterium*-mediated transformation method.

Genome editing methods such as the use of a CRISPR/Cas system might also be used to obtain a plant with the mutant allele of the invention.

The invention additionally provides a method of introducing another desired trait into a cucumber plant of the invention, which may comprise:
a) crossing a cucumber plant of the invention, with a second cucumber plant that may comprise a desired trait to produce F1 progeny;
b) selecting an F1 progeny that may comprise the desired trait;
c) crossing the selected F1 progeny with a cucumber plant of the invention to produce backcross progeny;
d) selecting backcross progeny which may comprise the desired trait and the allele of the ACO2 gene and trait of the invention; and
e) optionally repeating steps c) and d) one or more times in succession to produce selected fourth or higher backcross progeny that may comprise the desired trait and the allele of the ACO2 gene and trait of the invention. The invention includes a plant of the family of Cucurbitacea, in particular a cucumber plant, produced by this method.

The invention further provides a method for the production of a plant of the family of Cucurbitacea, in particular a cucumber plant, having the trait of producing only male flowers by using a doubled haploid generation technique on a plant which may comprise the mutant allele of the ACO2 gene of the invention to generate a doubled haploid line which may comprise the said trait.

In one embodiment, the invention relates to a method for producing a plant of the family of Cucurbitacea, in particular a cucumber plant, that has the trait of producing only male flowers, which may comprise crossing a first parent plant with a second parent plant and harvesting the resultant hybrid seed, wherein both the first parent plant and the second parent plant have at least one mutant allele of the ACO2 gene, which mutant allele when homozygously present in a plant, leads to producing male flowers only, and growing said seeds into plants having the trait of producing only male flowers.

The invention also relates to a method for the production of a plant of the family of Cucurbitacea, in particular a cucumber plant, having the trait of producing only male flowers by using a seed that may comprise the mutant allele of the ACO2 gene of the invention homozygously for growing the said plant.

In one embodiment, the invention relates to a method for the production of a plant of the family of Cucurbitacea, in particular a cucumber plant, having the trait of producing only male flowers by using tissue culture derived from a plant of the family of Cucurbitacea, in particular a cucumber plant, which may comprise the mutant allele of the ACO2 gene of the invention homozygously.

The invention furthermore relates to a method for the production of a plant of the family of Cucurbitacea, in particular a cucumber plant, having the trait of producing only male flowers by using vegetative reproduction of at least a part of a plant of the family of Cucurbitacea, in particular a cucumber plant, which may comprise the mutant allele of the ACO2 gene of the invention.

In one embodiment, the invention relates to a method for the production of a plant of the family of Cucurbitacea, in particular a cucumber plant, having the trait of producing only male flowers by using a method for genetic modification to introgress the mutant allele of the ACO2 gene of the invention into the plant. Genetic modification may comprise transgenic modification or transgenesis, using a gene from a non-crossable species or a synthetic gene, and cisgenic modification or cisgenesis, using a natural gene, coding for an (agricultural) trait, from the crop plant itself or from a sexually compatible donor plant.

The invention also relates to a breeding method for the development of cucumber plants that have the trait of producing only male flowers, wherein germplasm which may comprise the allele of the invention is used. Such germplasm is present in seed deposited under accession number NCIMB 42987.

In a further embodiment the invention relates to a method for the production of a plant of the family of Cucurbitacea, in particular a cucumber plant, having the trait of producing only male flowers, wherein progeny or propagation material of a plant which may comprise the ACO2 mutant allele of the invention is used as a source to introgress the said trait into another Cucurbitacea, in particular a cucumber, plant.

Furthermore, the invention relates to a method for selecting a cucumber plant that produces only male flowers, from a population of plants, which may comprise detecting a deletion of the nucleotide on position 278 of wild type ACO2 allele sequence SEQ ID NO: 1, in the genome of a plant in a population of plants, and selecting the plant which may comprise the deletion homozygously.

The selection may be done by using a marker that is linked to the mutant ACO2 allele sequence SEQ ID NO: 3.

The invention further relates to a method for identifying, detecting, genotyping, or selecting a cucumber plant which may comprise the ACO2 mutant allele of the invention, which may comprise determining, detecting, measuring, quantitatively or qualitatively ascertaining, or assaying a plant for the presence or absence of a genomic nucleotide sequence or a part thereof, wherein said sequence has in order of increased preference 95%, 96%, 97%, 98%, 99%, 100% sequence similarity to SEQ ID NO: 3, and wherein said sequence may comprise the deletion of the nucleotide on position 278 of wild type ACO2 allele sequence SEQ ID NO: 1.

Accordingly, the invention comprehends and includes characterizing a cucumber plant as carrying or not carrying the mutant allele of the ACO2 gene which may comprise determining or detecting or measuring or quantitatively or qualitatively ascertaining or assaying a cucumber plant for the presence or absence of a genomic nucleotide sequence or a part thereof, wherein said sequence has in order of increased preference 95%, 96%, 97%, 98%, 99%, 100% sequence similarity to SEQ ID NO: 3, said method may include extracting or obtaining DNA or RNA of the plant and analysis thereof as to the presence or absence therein of a nucleotide sequence or a part thereof, wherein said sequence has in order of increased preference 95%, 96%, 97%, 98%, 99%, 100% sequence similarity to SEQ ID NO: 3, and wherein said sequence may comprise the deletion of the nucleotide on position 278 of wild type ACO2 allele sequence SEQ ID NO: 1.

It is further understood that within the ambit of the invention one can also analyze expression product(s) such as a coding sequence or protein or parts thereof, of a cucumber plant to ascertain that from which the product(s) was/were expressed, from which it can be determined whether the plant has (or does not have) a genomic nucleotide sequence or a part thereof, with sequence similarity to SEQ ID NO: 3. Such a coding sequence would have in order of increased preference 80%, 81%, 82%, 83%, 84%, 85%, 86%, 87%, 88%, 89%, 90%, 91%, 92%, 93%, 94%, 95%, 96%, 97%, 98%, 99%, 100% sequence similarity to SEQ ID No:3, and wherein said sequence may comprise the deletion of the nucleotide on position 278 of wild type ACO2 allele sequence SEQ ID NO: 1. Such a protein has an amino acid sequence which has in order of increased preference 95%, 96%, 97%, 98%, 99%, 100% sequence similarity to SEQ ID No:4, and which may comprise the modification caused by the deletion of the nucleotide on position 278 of wild type ACO2 allele sequence SEQ ID NO: 1.

As used herein, "desirable traits" include but are not limited to e.g. improved yield, leaf shape, seed number, seed size, plant vigor, plant height, bolting, and resistance to one or more diseases or disease causing organisms. Any one of these desirable traits may be combined with the mutant ACO2 allele.

Table 1—The genomic sequences of the ACO2 gene, protein sequences encoded by the ACO2 gene, wild type and mutant versions.

| Name | Sequence |
|---|---|
| SEQ ID NO: 1<br>Wild type<br>nucleotide<br>sequence<br>(coding<br>sequence) | ATGGAGATGGATTTCCCTGTCATCAACATGAACAACCTCAATGG<br>CGAAAGCAGAGTATCTGTCCTGAACCAAATCAACGACGCCTGC<br>GAAAACTGGGGTTTTTTTGAGTTGGTGAATCATGGGATACCACA<br>TGAGCTGATGGACAAAGTGGAGAAGATGACAAAGGAACATTAT<br>AGAAAGTGCATGGAGCAGAGGTTTAAAGAAATGGTAGCTTCCA<br>AAGGGTTGGATTCAGTGGAAACTGAGATCAACGACACTGATTG<br>GGAAAGCACTTTTTTTTTACGCCATCTTCCAGTTTCAAACATGTC<br>AGAAATTGGTGATCTGGATGAGGAGTACAAGAAGGTGATGAAG<br>GAATTTGCAGCTGAACTGGAGAAATTAGCGGAGGAAATTCTGA<br>ACTTGTTGTGTGAGAATCTTGGGCTTGAAAAGGGGTATTTGAAA<br>AAAGTGTTTTATGGATCAAAAGGCCCAAACTTTGGGACAAAAG<br>TTAGCAATTACCCTCCATGTCCTAAACCTGAGCTTATTAAAGGA<br>CTTAGAGCCCATACCGATGCTGGTGGTCTTATTCTTCTGTTTCAA<br>GATGATAAAGTGAGTGGGCTTCAGCTGCTCAAAGATGGAAAAT<br>GGGTTGATGTTCCTCCGATGCATCACTCCATTGTTATCAATTTAG<br>GAGACCAGCTTGAAGTAATAACAAATGGAAAATACAAGAGTGT<br>AATGCACAGAGTGATAGCACAGGAGGATGGAAACAGAATGTCG<br>ATAGCATCATTCTACAATCCAGGAAACGACGCCGTAATCTATCC<br>GGCGCCGGCGCTGGTCGAGGGAGAGCAGGAGAAAACCAAACTT<br>TACCCAAAATTTGTGTTCGATGATTACATGAAGCTGTATATGGG<br>GCTTAAGTTTCAAGCAAAAGAGCCAAGGTTTGAGGCCATGAAA<br>GCCATGGAGTCCACCAATATCAATATGGGTCCAATTGCAACTGT<br>CTGA |
| SEQ ID NO: 2<br>Wild type<br>protein sequence | MEMDFPVINMNNLNGESRVSVLNQINDACENWGFFELVNHGIPHE<br>LMDKVEKMTKEHYRKCMEQRFKEMVASKGLDSVETEINDTDWES<br>TFFLRHLPVSNMSEIGDLDEEYKKVMKEFAAELEKLAEEILNLLCE<br>NLGLEKGYLKKVFYGSKGPNFGTKVSNYPPCPKPELIKGLRAHTD<br>AGGLILLFQDDKVSGLQLLKDGKWVDVPPMHHSIVINLGDQLEVIT<br>NGKYKSVMHRVIAQEDGNRMSIASFYNPGNDAVIYPAPALVEGEQ<br>EKTKLYPKFVFDDYMKLYMGLKFQAKEPRFEAMKAMESTNINMG<br>PIATV |
| SEQ ID NO: 3<br>Mutant<br>nucleotide<br>sequence (coding<br>sequence) | ATGGAGATGGATTTCCCTGTCATCAACATGAACAACCTCAATGG<br>CGAAAGCAGAGTATCTGTCCTGAACCAAATCAACGACGCCTGC<br>GAAAACTGGGGTTTTTTTGAGTTGGTGAATCATGGGATACCACA<br>TGAGCTGATGGACAAAGTGGAGAAGATGACAAAGGAACATTAT<br>AGAAAGTGCATGGAGCAGAGGTTTAAAGAAATGGTAGCTTCCA<br>AAGGGTTGGATTCAGTGGAAACTGAGATCAACGACACTGATTG<br>GGAAAGCACTTTTTTTTACGCCATCTTCCAGTTTCAAACATGTC<br>AGAAATTGGTGATCTGGATGAGGAGTACAAGAAGGTGATGAAG<br>GAATTTGCAGCTGAACTGGAGAAATTAGCGGAGGAAATTCTGA<br>ACTTGTTGTGTGAGAATCTTGGGCTTGAAAAGGGGTATTTGAAA<br>AAAGTGTTTTATGGATCAAAAGGCCCAAACTTTGGGACAAAAG<br>TTAGCAATTACCCTCCATGTCCTAAACCTGAGCTTATTAAAGGA<br>CTTAGAGCCCATACCGATGCTGGTGGTCTTATTCTTCTGTTTCAA<br>GATGATAAAGTGAGTGGGCTTCAGCTGCTCAAAGATGGAAAAT<br>GGGTTGATGTTCCTCCGATGCATCACTCCATTGTTATCAATTTAG<br>GAGACCAGCTTGAAGTAATAACAAATGGAAAATACAAGAGTGT<br>AATGCACAGAGTGATAGCACAGGAGGATGGAAACAGAATGTCG<br>ATAGCATCATTCTACAATCCAGGAAACGACGCCGTAATCTATCC<br>GGCGCCGGCGCTGGTCGAGGGAGAGCAGGAGAAAACCAAACTT<br>TACCCAAAATTTGTGTTCGATGATTACATGAAGCTGTATATGGG<br>GCTTAAGTTTCAAGCAAAAGAGCCAAGGTTTGAGGCCATGAAA<br>GCCATGGAGTCCACCAATATCAATATGGGTCCAATTGCAACTGT<br>CTGA |
| SEQ ID NO: 4<br>Mutant protein<br>sequence | MEMDFPVINMNNLNGESRVSVLNQINDACENWGFFELVNHGIPHE<br>LMDKVEKMTKEHYRKCMEQRFKEMVASKGLDSVETEINDTDWES<br>TFFYAIFQFQTCQKLVIWMRSTRR** |

* = stop codon

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

Identification of the ACO2 Gene Mutation in *Cucumis sativus*

In a study to create a new genetic map of the cucumber genome, a plant population was obtained of which some plants only produced male flowers. An analysis performed on this crossing population revealed a QTL on chromosome 6 that causes the plants that comprise the QTL to produce only male flowers. Sequencing of an internally developed marker revealed an insertion/deletion ("indel") present in the marker sequence. The particular sequence was polymorphic in the crossing population. The nucleotide sequence of the major QTL on chromosome 6 was identified by means of BLAST. The best BLAST hits for the sequence all resembled the sequence of the ACO2 *Cucumis sativus* gene.

Table 1 shows the coding sequence of ACO2 gene and the accompanying protein sequence, both the wild type and the mutant versions.

Example 2

Validation of a Marker that is Linked to the ACO2 Mutation

During further research, markers were tested to check whether they were linked to the indel found in the mutant ACO2 allele. It was found that marker CS05484 correlates 100% with the phenotype maleness (ability to produce only male flowers). To check the frequency of the indel, 54 internal parental lines were tested for the marker. The outcome was that 53 out of 54 internal parental lines were scored as "A", which is linked to the wildtype form of the ACO2 gene. Only one of the tested parental lines, the only parental line carrying the mutation in the ACO2 gene out of 54 internal parental lines, showed a "B" score.

Furthermore, various hybrid variety seeds of competitors/other breeding companies were tested and all of them scored "A" with this marker. Table 2 shows the parental lines and the hybrid varieties and their scores for the marker CS05484. Table 3 shows the wild type and mutant sequence of the marker CS05484, SEQ ID NO: 5 and SEQ ID NO: 6.

TABLE 2

Scores for marker CS05484 in various cucumber varieties and internal cucumber lines.

| Plot nr | Sample nr (reseq) | CS05484 |
|---|---|---|
| Cuc-1 | 25 | A |
| Cuc-2 | 26 | A |
| Cuc-3 | 27 | A |
| Cuc-4 | 28 | A |
| Cuc-5 | 29 | A |
| Cuc-6 | 30 | A |
| Cuc-7 | 31 | A |
| Cuc-8 | 32 | A |
| Cuc-9 | 33 | A |
| Cuc-10 | 34 | A |
| Cuc-13 | 37 | A |
| Cuc-14 | 38 | A |
| Cuc-16 | 40 | A |
| Cuc-17 | 41 | A |
| Cuc-18 | 42 | A |
| Cuc-19 | 43 | A |
| Cuc-20 | 44 | A |
| Cuc-21 | 45 | A |
| Cuc-22 | 46 | A |
| Cuc-23 | 47 | A |
| Cuc-24 | 48 | A |
| Cuc-25 | 73 | A |
| Cuc-26 | 74 | A |
| Cuc-27 | 75 | A |
| Cuc-29 | 77 | A |
| Cuc-30 | 78 | A |
| Cuc-31 | 79 | A |
| Cuc-32 | 80 | A |
| Cuc-33 | 81 | A |
| Cuc-34 | 82 | A |
| Cuc-35 | 83 | A |
| Cuc-36 | 84 | A |
| Cuc-37 | 85 | A |
| Cuc-38 | 86 | A |
| Cuc-39 | 87 | A |
| Cuc-40 | 88 | A |
| Cuc-41 | 89 | A |
| Cuc-42 | 90 | A |
| Cuc-43 | 91 | A |
| Cuc-44 | 92 | A |
| Cuc-45 | 93 | A |
| Cuc-46 | 94 | A |
| Cuc-47 | 95 | A |
| Cuc-48 | 96 | A |
| Cuc-49 | 116 | A |
| Cuc-50 | 117 | A |
| Cuc-51 | 118 | A |
| Cuc-52 | 119 | A |
| Cuc-53 | 120 | A |
| Cuc-54 | 121 | A |
| Cuc-55 | 122 | A |
| Cuc-56 | 123 | A |
| Cuc-57 | 124 | A |
| Cuc-61F | 127 | B |
| Cuc-62 | 128 | A |
| Cuc-63 | 129 | A |
| Cuc-64 | 130 | A |
| Cuc-65 | 131 | A |
| Cuc-66 | 132 | A |
| Cuc-67 | Bomber (Syngenta) | A |
| Cuc-68 | Legendario (Monsanto) | A |
| Cuc-69 | Vodich (Monsanto) | A |
| Cuc-70 | Espartaco (Monsanto) | A |
| Cuc-71 | SV 0091 (Monsanto) | A |
| Cuc-72 | Carlin (Enza) | A |
| Cuc-74 | Marcos (Enza) | A |
| Cuc-75 | Prior (Fito) | A |
| Cuc-76 | Caronte (Fito) | A |
| Cuc-77 | Kuiper (Nickerson Zwaan) | A |
| Cuc-78 | Medal (Nunhems) | A |
| Cuc-79 | Mirlo (Nunhems) | A |
| Cuc-80 | Misil (Nunhems) | A |
| Cuc-81 | Taray (Nunhems) | A |
| Cuc-82 | Tesoro (Nunhems) | A |
| Cuc-83 | Kantaka (Syngenta) | A |
| Cuc-84 | Triunfal (Syngenta) | A |
| Cuc-85 | Regalos (Syngenta) | A |
| Cuc-86 | Makedon (Syngenta) | A |

TABLE 3

Sequences of the marker CS05484, wild type and mutant version.

| | |
|---|---|
| SEQ ID NO: 5<br>CS05484<br>(wildtype) | AATGGTAGCTTCCAAAGGGTTGGATTCA<br>GTGGAAACTGAGATCAACGACACTGATT<br>GGGAAAGCACTTTTTTTTACGCCATCTT<br>CCAGTTTCAAACATGTCAGAAATTGGTGA<br>TCTGGATGAGGAGTACAAGAAGGTGATG<br>AAGGAATTTGCA |
| SEQ ID NO: 6<br>CS05484<br>(mutant) | AATGGTAGCTTCCAAAGGGTTGGATTCA<br>GTGGAAACTGAGATCAACGACACTGATT<br>GGGAAAGCACTTTTTTTT_ACGCCATCTT<br>CCAGTTTCAAACATGTCAGAAATTGGTGA<br>TCTGGATGAGGAGTACAAGAAGGTGATG<br>AAGGAATTTGCA |

The invention is further described by the following numbered paragraphs:

1. A mutant allele of the ACO2 gene comprising a mutation in the DIOX_N domain of the wild type ACO2 gene nucleotide sequence of SEQ ID NO: 1, wherein the mutation if homozygously present in the genome of a cucumber plant, results in a cucumber plant producing only male flowers.
2. The mutant allele of the ACO2 gene of paragraph 1, wherein the mutation in the DIOX_N domain of the nucleotide sequence SEQ ID NO: 1 leads to a change in the wild type ACO2 protein sequence of SEQ ID NO: 2.
3. The mutant allele of the ACO2 gene of paragraph 1 or 2, wherein the mutation in the DIOX_N domain of the nucleotide sequence SEQ ID NO: 1 leads to a premature stop codon.
4. The mutant allele of the ACO2 gene of any of the paragraphs 1-3, wherein the mutation in the DIOX_N domain of the nucleotide sequence SEQ ID NO: 1 comprises a deletion.
5. The mutant allele of the ACO2 gene of paragraph 4, wherein the deletion is a deletion of at least a single thymine nucleotide.
6. The mutant allele of the ACO2 gene of any one of the paragraphs 1-5, wherein the mutation is a deletion of the nucleotide on position 278 in the wild type nucleotide sequence of SEQ ID NO: 1.
7. The mutant allele of the ACO2 gene of any one of the paragraphs 1-6, comprising SEQ ID NO: 3.
8. A cucumber plant, comprising the mutant allele of the ACO2 gene of any of the paragraphs 1-7.
9. The cucumber plant of paragraph 8, comprising the mutant allele of the ACO2 gene homozygously and which plant produces only male flowers.
10. The cucumber plant of paragraph 8 or 9, wherein the cucumber plant is an agronomically elite plant.
11. The cucumber plant of any one of the paragraphs 8-10, wherein the cucumber plant is a hybrid variety plant or an inbred line plant.
12. A cucumber seed comprising the mutant allele of the ACO2 gene of any of the paragraphs 1-7.
13. The cucumber seed of paragraph 12, comprising the mutant allele of the ACO2 gene homozygously, and wherein a plant grown from said seed produces only male flowers.
14. Propagation material comprising the mutant allele of the ACO2 gene of any of the paragraphs 1-7, and wherein the propagation material is selected from a microspore, a pollen, an ovary, an ovule, an embryo, an embryo sac, an egg cell, a cutting, a root, a hypocotyl, a cotyledon, a stem, a leaf, a flower, an anther, a seed, a meristematic cell, a protoplast, or a cell, or a tissue culture thereof.
15. Propagation material of paragraph 14, comprising the mutant allele of the ACO2 gene homozygously, and wherein a plant derived from said propagation material produces only male flowers.
16. Marker for identifying a cucumber plant comprising a mutant ACO2 allele, wherein the marker comprises a deletion of a nucleotide on position 278 of the wild type ACO2 gene nucleotide sequence of SEQ ID NO: 1.
17. Marker of paragraph 16, comprising SEQ ID NO: 6.
18. Method for obtaining a plant that produces only male flowers, comprising:
    a) crossing a plant comprising the mutant allele of the ACO2 gene of any one of the paragraphs 1-7 with a plant comprising or not comprising the mutant allele of the ACO2 gene, to obtain an F1 population;
    b) performing one or more rounds of selfing and/or crossing a plant from the F1 to obtain a further generation population;
    c) selecting a plant that produces only male flowers and comprises the mutant allele of the ACO2 gene homozygously.
19. Method for selecting a cucumber plant that produces only male flowers from a population of plants, comprising detecting a deletion of the nucleotide on position 278 of SEQ ID NO: 1 in the genome of a plant in a population of plants, and selecting the plant comprising the deletion homozygously.
20. Method for identifying, detecting, genotyping or selecting a cucumber plant comprising the mutant allele of the ACO2 gene of any one of the paragraphs 1-7, comprising determining, detecting, measuring, quantitatively or qualitatively ascertaining or assaying a plant for the presence or absence of a genomic nucleotide sequence or a part thereof, wherein said sequence has in order of increased preference 95%, 96%, 97%, 98%, 99%, 100% sequence similarity to SEQ ID NO: 3.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. An agronomically elite, or a hybrid variety or inbred cucumber plant having a mutant allele of the 1-aminocyclopropane-1-carboxylate oxidase 2 (ACO2) gene,
   wherein the mutant allele comprises a deletion of the nucleotide at position 278 in the wild type nucleotide sequence of SEQ ID NO: 1, or having a mutant allele of the 1-aminocyclopropane-1-carboxylate oxidase 2 (ACO2) gene comprising SEQ ID NO: 3,
   wherein the deletion of the nucleotide position at 278 in the wild type nucleotide sequence SEQ ID NO: 1 leads to a premature stop codon, and
   wherein the mutant allele, if homozygously present in the genome of a cucumber plant, results in a cucumber plant producing only male flowers.

2. An agronomically elite, or a hybrid variety or inbred cucumber plant having a mutant allele of the 1-aminocyclopropane-1-carboxylate oxidase 2 (ACO2) gene,
   wherein the mutant allele comprises a deletion of the nucleotide at position 278 in the wild type nucleotide sequence of SEQ ID NO: 1, or having a mutant allele of the 1-aminocyclopropane-1-carboxylate oxidase 2 (ACO2) gene comprising SEQ ID NO: 3,
   wherein the deletion of the nucleotide position at 278 in the wild type nucleotide sequence SEQ ID NO: 1 leads to a premature stop codon, and
   wherein the mutant allele is homozygously present in the genome of a cucumber plant and results in a cucumber plant producing only male flowers, and
   wherein representative seed of a cucumber plant having the mutant allele of the ACO2 gene was deposited under NCIMB Accession No. 42987.

3. The cucumber plant of claim 1, wherein in the mutant allele of the ACO2 gene, the deletion is a deletion of at least a single thymine nucleotide.

4. The cucumber plant of claim 1, wherein the mutant allele of the ACO2 gene is homozygously present, and wherein the cucumber plant produces only male flowers.

5. A cucumber seed comprising a mutant allele of the ACO2 gene,
   wherein the mutant allele comprises a deletion of the nucleotide at position 278 in the wild type nucleotide sequence of SEQ ID NO: 1, or having a mutant allele of the 1-aminocyclopropane-1-carboxylate oxidase 2 (ACO2) gene comprising SEQ ID NO: 3,
   wherein the deletion of the nucleotide position at 278 in the wild type nucleotide sequence SEQ ID NO: 1 leads to a premature stop codon, and
   wherein the mutant allele, if homozygously present in the genome of a cucumber plant grown from said seed, results in a cucumber plant producing only male flowers.

6. The cucumber seed of claim 5, wherein the ACO2 gene is homozygously present and wherein a plant grown from said seed produces only male flowers.

7. A propagation material suitable for producing the plant of claim 1, wherein the propagation material comprises the mutant allele of the ACO2 gene, and
   wherein the propagation material is selected from a microspore, a pollen, an ovary, an ovule, an embryo, an embryo sac, an egg cell, a cutting, a root, a hypocotyl, a cotyledon, a stem, a leaf, a flower, an anther, a seed, a meristematic cell, a protoplast, or a cell, or a tissue culture.

8. The propagation material of claim 7, wherein the mutant allele of the ACO2 gene is homozygously present, and wherein a plant derived from said propagation material produces only male flowers.

9. A marker for identifying a cucumber plant comprising a mutant ACO2 allele, wherein the marker comprises a deletion of a nucleotide at position 278 of the wild type ACO2 gene nucleotide sequence of SEQ ID NO: 1, and the marker has the sequence of SEQ ID NO: 6.

10. A method for obtaining a cucumber plant that produces only male flowers, comprising:
    a) crossing the cucumber plant of claim 1 with a cucumber plant comprising or not comprising the mutant allele of the ACO2 gene, to obtain an F1 population;
    b) performing one or more rounds of selfing and/or crossing a plant from the F1 to obtain a further generation population;
    c) selecting a plant that produces only male flowers and comprises the mutant allele of the ACO2 gene homozygously.

11. A method for selecting a cucumber plant that produces only male flowers from a population of cucumber plants, comprising detecting a deletion of the nucleotide at position 278 of SEQ ID NO: 1 in the genome of the cucumber plant in a population of cucumber plants, and selecting the cucumber plant comprising the deletion homozygously.

12. A method for identifying, detecting, genotyping or selecting the cucumber plant of claim 1, comprising determining, detecting, measuring, quantitatively or qualitatively ascertaining or assaying a cucumber plant for the presence of a genomic nucleotide sequence or a part thereof, wherein said genomic nucleotide sequence has at least 95% sequence identity to SEQ ID NO: 3, and comprises a deletion of a nucleotide at position 278 of the wild type ACO2 gene nucleotide sequence SEQ ID NO: 1.

13. The cucumber plant of claim 1, wherein the mutant allele of the ACO2 gene confers a L93Y mutation to a protein encoded by the ACO2 gene at position 93 of SEQ ID NO: 2.

* * * * *